United States Patent [19]

Nardella

[11] Patent Number: 5,383,876
[45] Date of Patent: Jan. 24, 1995

[54] FLUID COOLED ELECTROSURGICAL PROBE FOR CUTTING AND CAUTERIZING TISSUE

[75] Inventor: Paul C. Nardella, North Easton, Mass.

[73] Assignee: American Cardiac Ablation Co., Inc., Taunton, Mass.

[21] Appl. No.: 216,069

[22] Filed: Mar. 22, 1994

Related U.S. Application Data

[63] Continuation of Ser. No. 975,866, Nov. 13, 1992.

[51] Int. Cl.⁶ ............................................. A61B 17/39
[52] U.S. Cl. ....................................... 606/49; 606/50; 606/37; 606/39; 606/40
[58] Field of Search ........................ 606/37, 38, 39, 40, 606/41, 42, 43, 44, 45, 46, 47, 48, 49, 50

[56] References Cited

U.S. PATENT DOCUMENTS

| | | |
|---|---|---|
| 641,184 | 3/1875 | Kidder . |
| 1,983,669 | 4/1933 | Kimble . |
| 3,572,344 | 12/1968 | Bolduc . |
| 4,532,924 | 8/1985 | Auth et al. . |
| 4,562,838 | 1/1986 | Walker . |
| 4,637,392 | 1/1987 | Sorochenko . |
| 4,674,499 | 6/1987 | Pao . |
| 4,823,791 | 4/1989 | D'Amelio et al. . |
| 4,943,290 | 7/1990 | Rexroth et al. . |
| 5,006,119 | 4/1991 | Acker et al. . |
| 5,035,695 | 7/1991 | Weber, Jr. et al. ................ 606/42 |
| 5,047,026 | 9/1991 | Rydell ................................. 606/39 |
| 5,057,107 | 10/1991 | Parins et al. ....................... 606/48 |
| 5,071,418 | 12/1991 | Rosenbaum ....................... 606/42 |
| 5,085,657 | 2/1992 | Ben-Simhon . |
| 5,167,659 | 12/1992 | Ohtomo et al. . |
| 5,195,959 | 3/1993 | Smith . |

OTHER PUBLICATIONS

*Endoscopic Heat Probe Coagulation*, David C. Auth, Ph.D., P.E.

Primary Examiner—David M. Shay
Assistant Examiner—Sonya C. Harris
Attorney, Agent, or Firm—Lahive & Cockfield

[57] ABSTRACT

An electrosurgical probe is disclosed which provides the ability to both cut and cauterize tissue. The probe includes at least one cauterization electrode mounted upon a distal portion of the electrode and adapted to deliver electrosurgical energy to tissue. Further, a central lumen is disposed within the probe. The lumen is adapted to accommodate the flow of fluid from a remote source to tissue through an outlet port in the distal end of the probe. Also, the lumen houses a cutting electrode which is selectively deployable. Both cauterization and coagulation can be conducted in a bipolar mode. The flow of fluid through the lumen serves to limit the heat transfer from the cauterization electrode to adjacent tissue to an extent sufficient to prevent the sticking of tissue to the probe. In another embodiment the probe is adapted only for cauterization and does not include a cutting electrode.

21 Claims, 4 Drawing Sheets

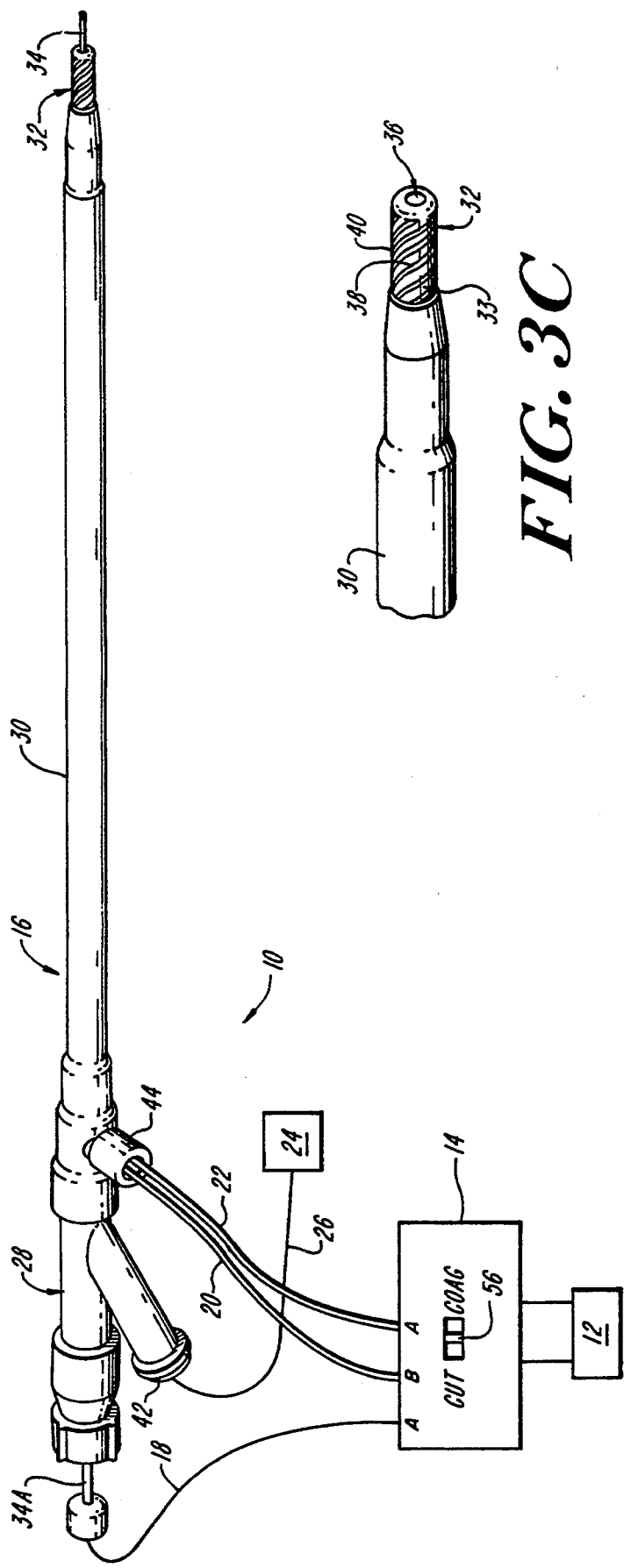

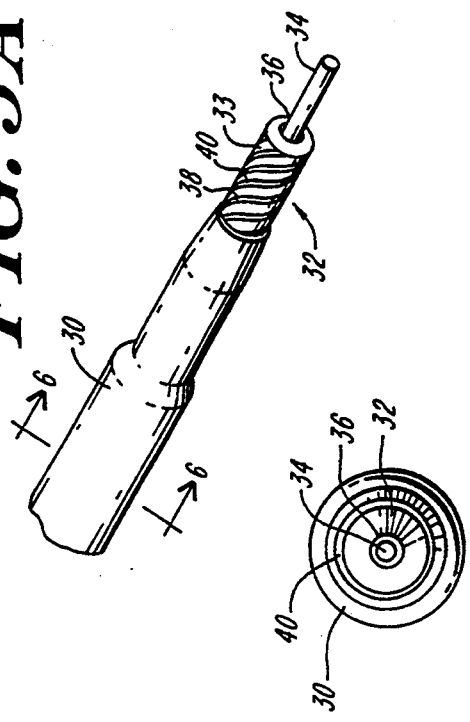
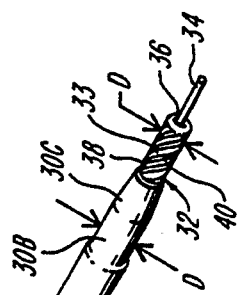
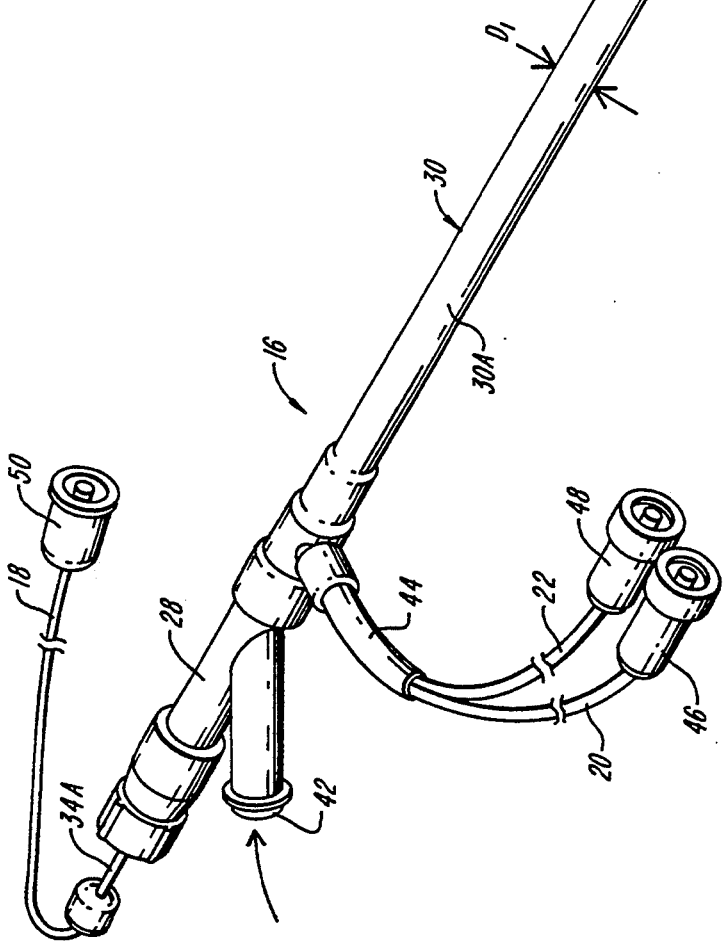

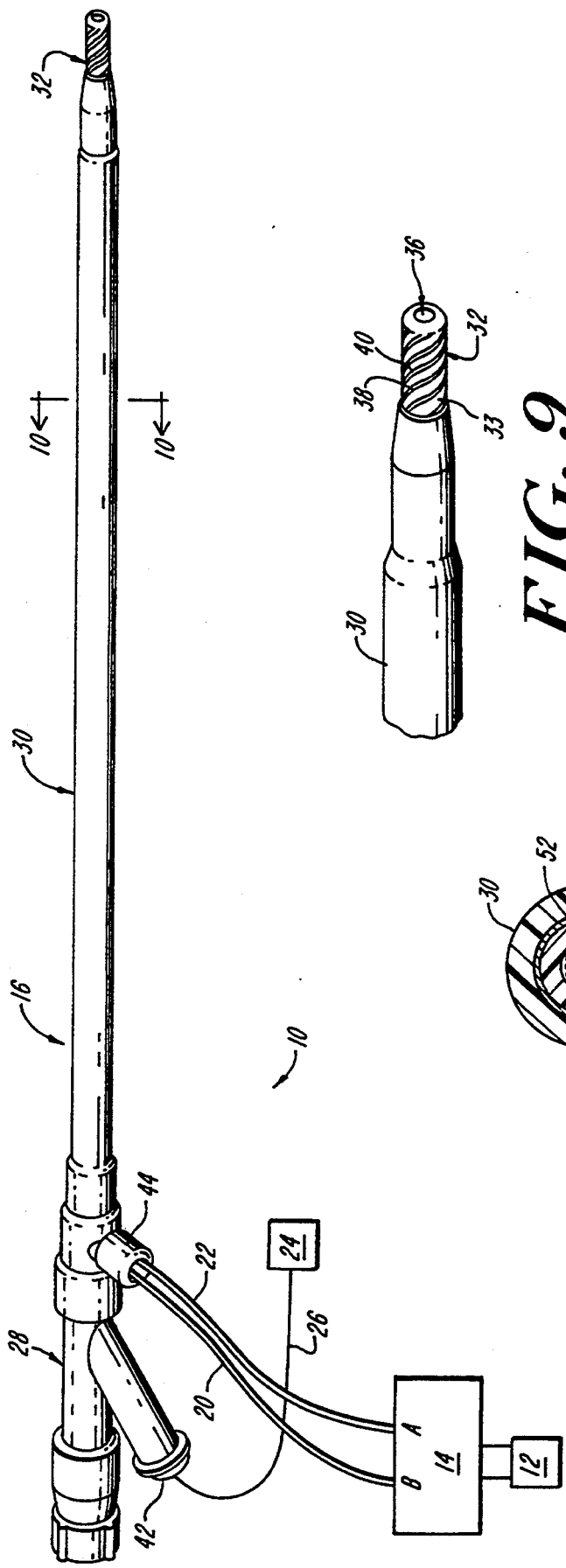

5,383,876

FLUID COOLED ELECTROSURGICAL PROBE FOR CUTTING AND CAUTERIZING TISSUE

BACKGROUND OF THE INVENTION

This application is a continuation of application Ser. No. 07/975,866 filed on Nov. 13, 1992.

The invention relates to an electrosurgical device which is able to be used for tissue cauterization and cutting.

During the course of surgical procedures it is often necessary to cauterize or coagulate tissue to control bleeding. Electrosurgical devices are known which utilize electrical current for tissue cauterization. U.S. Pat. Nos. 1,983,669 and 4,637,392 disclose electrical cauterization devices in which electrodes are disposed about the surface of a probe. Tissue is heated and coagulation is effected by delivering electrosurgical energy to tissue through the electrodes. Among the drawbacks of such devices is the potential that the electrodes will become overly heated, thus prematurely dessicating the tissue and causing the tissue to stick to the electrodes. This can result in further bleeding upon disengagement of the electrodes from the tissue, and the need to remove tissue from the electrode before continuing to use the device. Moreover, it can be inconvenient to use such cauterization devices during certain surgical procedures because cutting and cauterization must be performed with separate instruments.

Other specialized electrocautery devices are also known. For example, U.S. Pat. No. 4,532,924 discloses a multipolar device that can be endoscopically delivered to a site of internal bleeding. The device also includes a lumen for delivering a fluid to enhance visibility at the target area.

In addition, surgical devices are known that utilize active electrodes to perform cutting procedures. These devices are useful for cutting tissue, but are not well adapted for tissue cauterization. In most instances, surgeons must change surgical instruments to cauterize tissue following a cutting procedure. Although inconvenient, the need to change surgical instruments for cutting and cauterization procedures is usually not a serious problem with respect to general surgical procedures. However, it becomes a greater problem during microsurgical procedures as it can be time consuming and difficult to re-position a separate cauterization instrument at the appropriate target site.

There is thus a need for a single surgical device that can perform tissue cutting procedures and tissue cauterization procedures virtually simultaneously. Such a device would be useful in that it would eliminate the need to change surgical tools to conduct cutting and cauterization procedures, and would enable a surgeon to quickly control bleeding. A device of this type would be well suited to general surgical procedures as well as to microsurgical procedures.

Accordingly, it is an object of the invention to provide a surgical device that performs both cutting and cauterization procedures. A further object is to provide such a device that is adapted for use with general surgical procedures and with microsurgical procedures. It is also an object to provide such a device that is adapted to control the temperature of energy-delivering electrodes during cauterization to prevent or minimize the sticking of tissue to cauterization electrodes. Another object of the invention is to provide such a device that can be used in a bipolar mode for both cauterization and tissue cutting procedures. Other objects of the invention will be apparent upon reading the description which follows.

SUMMARY OF THE INVENTION

In one embodiment the present invention comprises an electrosurgical device that includes an elongate surgical probe member having disposed about a portion of its outer surface dual cauterization electrodes that are electrically isolated from each other. In one embodiment the cauterization electrodes may be helically oriented about the outer surface of the probe member. A longitudinally oriented lumen extends through the member and is adapted to deliver a fluid through the member from a fluid source. The lumen has at least one outlet port, preferably at the distal end of the member, through which the fluid can be discharged. The device also includes a selectively deployable cutting electrode that is able to be retracted within the lumen when not in use, and to be extended from the lumen upon deployment. The fluid delivered through the lumen serves both to cool the cauterization electrodes during cauterization, and to irrigate the surgical site.

The device is used in conjunction with an electrosurgical generator that supplies electrosurgical energy to the cauterization electrodes and to the cutting electrode. Switches are provided to enable a surgeon to switch easily between the cutting and coagulation modes, and to selectively deliver fluid through the lumen at desired flow rates.

When used for cauterization the device can function in a bipolar mode with the dual cauterization electrodes being electrically isolated from each other. The device also may be used as a bipolar surgical device for performing cutting procedures with the cutting electrode serving to cut tissue, and the cauterization electrodes serving as return electrodes.

In another embodiment the device serves only as a cauterization probe and does not include a cutting electrode.

The device is useful for general surgical applications in which the cutting and cauterization probe directly accesses a target site through a percutaneous incision located proximal to the target site. In addition, the probe may be manufactured in dimensions suitable for use in microsurgical procedures where the probe can be delivered to the target during arthroscopic, endoscopic, or laproscopic surgery.

BRIEF DESCRIPTION OF THE DRAWINGS

FIG. 1 is a schematic view of an electrosurgical cutting and coagulation system constructed according to the present invention.

FIG. 2 is a perspective view of an electrosurgical probe useful with the system illustrated in FIG. 1.

FIG. 3A is a perspective view of a forward portion of the electrosurgical probe illustrated in FIG. 2.

FIG. 3B is a front end view of the probe illustrated in FIG. 3A.

FIG. 3C is a perspective view of the probe illustrated in FIG. 3A, with the cutting electrode in the retracted position.

FIG. 8 is schematic view of an electrosurgical cauterization system according to the present invention.

FIG. 9 is a perspective view of a forward portion of an electrosurgical cauterization probe useful with the system of FIG. 8.

FIG. 10 is a sectional view, allow lines 10—10 of the electrosurgical cauterization probe of FIG. 8.

DETAILED DESCRIPTION OF THE INVENTION

Figure 4:
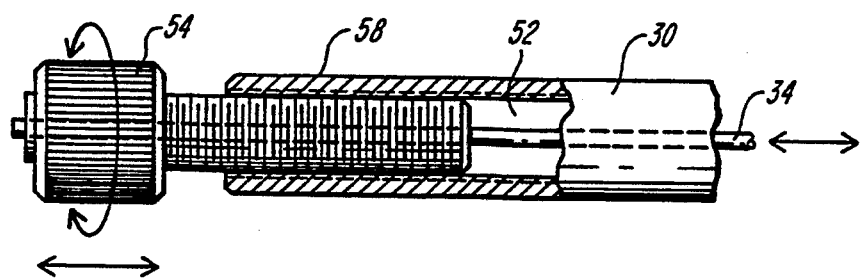
FIG. 4 is a side view, partially cut away, of a rear portion of the electrosurgical probe of FIG. 2, illustrating a knob for controlling the extension and retraction of the cutting electrode.

FIG. 1 illustrates the electrosurgical cutting and coagulation system 10 of the present invention. The system 10 comprises a radio frequency energy source 12, a control unit 14, in electrical communication with the energy source, and an electrosurgical probe 16. The control unit 14 is in electrical communication with probe 16 through electrode leads 18, 20, 22. Further, a fluid source 24 communicates a fluid to probe 16 through conduit 26.

The electrosurgical cutting and cauterization probe 16 is further illustrated in FIGS. 2 through 3C. As illustrated, probe 16 has a handle portion 28 at its proximal end and an elongate member 30 that extends from the handle portion. The distal end of elongate member 30 is somewhat tapered and includes a cauterization tip 32 and a retractable cutting electrode 34. Cutting electrode 34 is able to extend from, or to be retracted within, a substantially circular orifice 36 which preferably is disposed in the distal end of cauterization tip 32. The exposed outer surface 33 of the cauterization tip 32 includes dual cauterization electrodes 38, 40. Preferably, cauterization electrodes 38, 40 are helically oriented about the surface 33 of cauterization tip 32. However, other orientations for electrodes 38, 40 are possible as well.

The handle portion 28 of probe 16 includes a fluid inlet port 42 that communicates with fluid source 24 through conduit 26. Electrode leads 20 and 22 emerge from a cuff 44 on the handle portion 28 of the probe. The proximal ends of leads 20, 22 have connectors 46, 48, which are matable with control unit 14. The distal ends of leads 20 and 22 connect to cauterization electrodes 38 and 40, respectively.

Cutting electrode 34 extends throughout the length of probe 16, and preferably has a length greater than the probe itself so that it is able to emerge both from the distal end of member 30 and the proximal end of handle 28. An electrode lead 18, having connector 50, connects the proximal end 34A of cutting electrode 34 to control unit 14. Cutting electrode 34 preferably is coated with an insulating material over its entire length, except for its extreme distal end which is uncoated so as to deliver electrosurgical energy to tissue. Suitable insulating materials include polymers such as polyvinylidene fluoride, polytetrafluoroethylene, fluorinated ethylene-propylene polymers, polyethylene, and others known to be suitable for use in medical applications.

Figure 5:
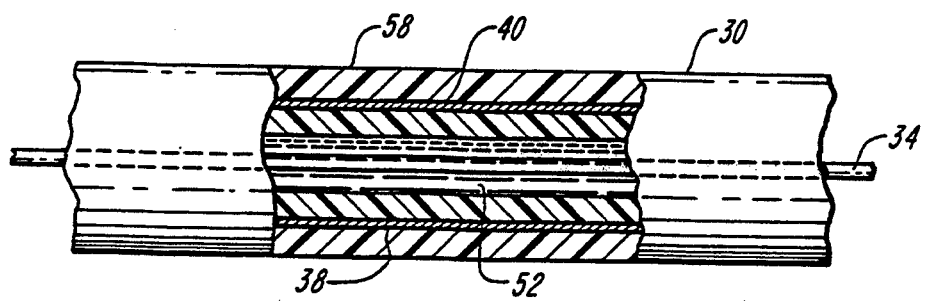
FIG. 5 is a side view, partially cut away, illustrating a portion of the electrosurgical probe of FIG. 2 constructed according to the present invention.
Figure 6:
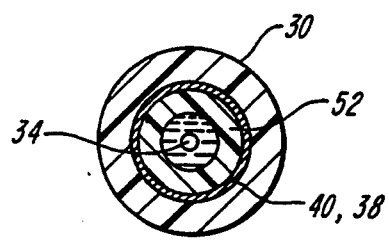
FIG. 6 is a sectional view along lines 6—6 of the probe illustrated in FIG. 3A.

Referring to FIGS. 4, 5, and 6, lumen 52 preferably is centrally located within probe 16 and extends throughout the length of the handle portion 28 and elongate member 30, along the longitudinal axis of the probe. The inlet port 42 provides a passageway for fluid to be communicated from conduit 26 to lumen 52. A fluid from source 24 is thus able to be communicated to inlet port 42 to enable fluid to be delivered through the lumen to the orifice 36 where it is discharged from the probe to contact tissue.

Figure 7:
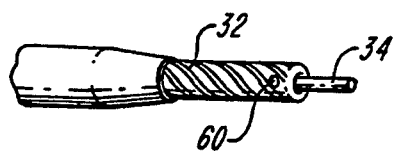
FIG. 7 is an alternative embodiment of the electrosurgical probe illustrated in FIG. 3A, having a side-mounted fluid outlet port.

In an alternative embodiment, illustrated in FIG. 7, a side-mounted orifice 60, in fluid communication with lumen 52, may be used to discharge fluid to adjacent tissue. Orifice 60 may be used alone, or in combination with orifice 36. Also, orifice 60 may, if desired, be paired with one or more additional side-mounted orifices (not shown).

As noted, cutting electrode 34 is positioned within and extends over the entire length of lumen 52. The selectively deployable nature of cutting electrode 34 is advantageous in that electrode 34 can be deployed for a cutting procedure and retracted during cauterization.

Deployment of electrode 34 can be controlled by a suitable mechanism preferably mounted on the handle portion 28 of probe 16. FIG. 4 illustrates a thumbscrew 54, mounted upon the proximal end of handle 28, which can be used to control the retraction and extension of the cutting electrode 34. Alternatively, as shown in FIG. 1, an excess length of electrode 34 may extend from the proximal end of handle 28 so as to be manually manipulated to regulate the length of electrode 34 extending from orifice 36. A variety of other length controlling mechanisms may be utilized as well.

In one embodiment cutting electrode 34 may be biased either to an extended or retracted position. The biasing force may be overcome by the mechanism used to control the extension/retraction of electrode 34.

The dimensions of the probe 16 are such that it is suitable for use in arthroscopic, endoscopic, laproscopic, and general surgery. Preferably, the length of the probe is approximately 10 to 18 inches. The diameter of member 30 can vary within a range of dimensions known in the art to be suitable for the intended use of the probe. In a preferred embodiment, the diameter is not constant along the entire length of member 30. Member 30 preferably has approximately 3 distinguishable but integral sections which have slightly differing diameters. As illustrated in FIG. 2, a proximal section 30A of the member 30 is the longest segment and has the largest diameter $D_1$. Adjacent this section is portion 30B of member 30, having a slightly smaller diameter $D_2$. The diameter of region 30C tapers over its entire length, terminating in cauterization tip 32 which has a diameter $D_3$. Generally, the diameter $D_1$ ranges from approximately 10 to 20 French (0.13 to 0.26 inch). Diameter $D_2$ ranges from 7 to 15 French while $D_3$ ranges from about 5 to 12 French.

The diameter of cutting electrode 18 can also vary, and its size depends to a large extent upon the diameter of lumen 52. One requirement of the lumen diameter is that it be sufficient to accommodate the flow of fluid while electrode 18 is disposed within the lumen. Generally, the lumen diameter is in the range of 3 to 7 French, while the diameter of electrode 34 ranges from 1 to 3 French.

The probe 16 of the present invention can be manufactured of a variety of materials, including polyolefins and nylons, that are known to be suitable for use in medical applications. The outer wall 58 of member 30 preferably is manufactured of an insulating polymeric material of the type well known in the art and suitable for use in medical applications.

The cutting electrode 34 and cauterization electrodes 38, 40 preferably are made from a highly conductive material such as gold, silver or platinum. The conductive material from which the electrodes are made can be a solid material or, alternatively, a plating which is deposited upon an insulating material such as a polymer. The cutting electrode should have sufficient rigidity, tensile strength and compressive strength to enable it to be extended from and retracted within the probe 16.

As noted, the probe 16 of the present invention is useful in general surgical procedures as well as in laproscopic, arthroscopic, and endoscopic surgical procedures. A significant advantage of probe 16 is that it represents a single instrument which can perform both cauterization and cutting procedures in a bipolar mode. Moreover, cauterization with probe 16 is more effective because the fluid flow through lumen 52 prevents electrodes 38 and 40 from transferring excessive thermal energy to tissue.

In operation, the probe may be inserted through an incision and directed to the location at which the surgical procedure is to be performed. Cutting electrode 34 can be extended from within lumen 52 once the probe reaches the surgical site. Thereafter, electrosurgical energy can be delivered between electrode 34 and one or both of electrodes 38, 40 (serving as return electrodes) to cut tissue. Control of bleeding can be effected utilizing cauterization tip 32 and cauterization electrodes 38 and 40. To do so, tip 32 is positioned in contact with tissue requiring cauterization and electrosurgical energy is delivered between electrodes 38 and 40 upon changing the mode of operation from cutting to coagulation, using, for example, switch 56 on control unit 14. This cauterization procedure can be bipolar in that one of electrodes 38 and 40 serves as an active, energy delivering electrode, while the other serves as a return electrode.

FIGS. 8 through 10 illustrate an alternative embodiment of the invention in which system 10 serves only to cauterize tissue. The probe is similar in construction to that illustrated in FIGS. 1 through 7, but it does not include a cutting electrode. Although lumen 52 is illustrated as being centrally disposed within member 30, it is understood that the lumen need not be disposed within member 30, but instead can be appended to member 30.

During cauterization procedures, and optionally during cutting as well, fluid is delivered through lumen 52 at a desired rate. The delivery of fluid serves two purposes. First, the fluid acts to limit the heat transfer from cauterization electrodes 38, 40 to adjacent tissue to an extent that tissue does not become overly heated by the electrodes, causing tissue and/or coagulant to stick to tip 32. This enables more effective and convenient cauterization. The fluid delivered to tissue can also serve as an irrigant to improve the visibility in the area subject to surgery and to remove any debris from the surgical site.

The fluid flow rate may be constant or variable. Preferably, the flow rate is variable and occurs only when energy is delivered to effect cauterization and preferably ranges from approximately 1 to 50 ml/minute. One skilled in the art will readily appreciate that it may be desirable to use a somewhat higher flow rate.

One of ordinary skill in the art will appreciate that the fluid flow rate depends on a number of variables, including the temperature of the fluid and the amount of power delivered to the cauterization electrode. The flow rate should be effective to control the temperature of the cauterization electrode, but should not be so high as to destroy tissue. The electrode temperature should be maintained below about 60° C., and more preferably below about 46° C. The temperature of the fluid may range from quite cold (e.g., about 4° C.) to about room temperature or higher (e.g., about 27° C.).

Flow rate can be manually adjusted or can be controlled by one or more feedback mechanisms that monitor tissue impedance and/or electrode temperature. A suitable feedback mechanism is disclosed in copending U.S. patent application Ser. No. 07/975,866, filed concurrently herewith and entitled Fluid Cooled Electrosurgical Cauterization System, which is incorporated herein by reference.

One skilled in the art will readily appreciate that certain surgical procedures will be able to tolerate more fluid flow while others will be able to tolerate less. The fluid flow rate can be adjusted to accommodate the requirements of a variety of surgical procedures.

The fluid source 24 may communicate with a valve or pump mechanism (not shown) which controls the flow rate of fluid through lumen 52. The flow rate can be constant at a predetermined rate, such as about 30 ml/minute, which generally is sufficient to limit the temperature of electrodes 38, 40 and cauterization tip 32.

Virtually any generator able to provide electrosurgical energy for medical applications may be used with the present invention. Preferably, the generator 12 is a voltage determinative, low source impedance generator that provides radio frequency energy. A preferred generator is able to supply up to 3 amps of current and has an impedance value of less than 10 ohms.

The energy supplied by the generator to the control unit 14 and to probe 16 is preferably in the radio frequency (RF) range. Although virtually any frequency in the RF range may be supplied to probe 16, the preferred range is about 500 to 700 KHz, and most preferably about 550 KHz.

As illustrated in FIG. 1, RF energy is provided to a control unit 14 from a generator 12. The control unit 14 includes switching mechanism 56 which enables a surgeon to control to mode of operation of the probe. Moreover, additional switches (not shown) mounted on or remote from unit 14 may be used to control the delivery of energy and the magnitude of the delivered energy.

The energy requirements of the probe are dynamic and will vary upon the impedance value of tissue which is being treated, and upon whether the tissue is being coagulated or cut. The impedance of tissue varies among tissue types and the amount of blood present in or around the tissue. The amount of current delivered by the probe to tissue thus depends on the impedance of the tissue. Where the tissue contacted has a lower impedance value, more current will be delivered to the tissue through the clip, and, conversely, less current will be delivered where the tissue has a higher impedance value. The current delivered during cutting procedures utilizing electrode 34 generally ranges between 0.2 amps and 3 amps. The voltage applied to tissue for such cutting procedures is between about 60 and 1000 volts rms. Current delivered during coagulation is generally in the range of 0.25 to 1.0 amp., and coagulation voltages is in the range of about 10 volts to about 50 volts rms.

It is understood that various modifications may be made to the invention described above without departing from the scope of the claims. For example, rather than operating in the bipolar mode, the cutting and coagulation each may be performed in a monopolar mode with the use of a remote ground pad. Also, the mode of operation may be controlled by the use of a foot pedal rather than a switch mounted on control unit 14.

What is claimed is:

1. An electrosurgical device, comprising:
   an elongate surgical probe member having disposed about a distal portion of the outer surface thereof at least one cauterization electrode;
   a longitudinally oriented, centrally disposed lumen extending through the member, the lumen adapted to deliver a fluid through the member to be discharged through an outlet port disposed in a distal portion of the member;
   a selectively deployable cutting electrode positioned within the lumen alternately deployable between an extended position, when the electrode extends from the lumen, and a retracted position, when the electrode is retracted within the lumen during periods of non-use, the electrode being of such diameter that it does not fully occlude the lumen; and
   a means for delivering electrosurgical energy through the device to the cauterization electrode and to the cutting electrode.

2. The device of claim 1 further comprising first and second cauterization electrodes disposed about the distal portion of the device outer surface, the first and second electrodes being electrically isolated from one another, wherein the first electrode serves as an active, energy delivering electrode and the second electrode serves as a ground electrode.

3. The device of claim 2 wherein the first and second cauterization electrodes are each helically oriented and disposed about the outer surface of a distal portion of the member.

4. The device of claim 3, wherein the means for delivering electrosurgical energy communicates with an electrosurgical generator.

5. The device of claim 4 wherein the cutting electrode features an insulating coating along its length, except for the distal end thereof which is uncoated and able to contact and electrically communicate with tissue when in the extended position to effect the cutting of tissue.

6. The device of claim 3 wherein the helical coagulation electrodes are constructed of or are coated with a conductive material selected from the group consisting of gold, silver, and platinum.

7. The device of claim 1 wherein the cauterization electrode is helically oriented about the outer surface of a distal portion of the member.

8. The device of claim 1 wherein the outlet port is disposed at the distal tip of the member.

9. The device of claim 1 wherein the probe member further comprises a first outlet port mounted on the distal tip of the member for discharging a fluid in a direction substantially parallel to the lumen, and at least one additional outlet port mounted in a side wall of the lumen.

10. The device of claim 1 wherein the cutting electrode is constructed of or coated with a conductive material selected from the group consisting of gold, silver, and platinum.

11. The device of claim 1 wherein the diameter of the cutting electrode is in the range of about 1 to 3 French.

12. The device of claim 1 further comprising a means for controlling the deployment of the cutting electrode.

13. An electrosurgical cutting and coagulation system comprising
   an elongate surgical probe member having disposed about a distal portion of the outer surface thereof at least one cauterization electrode;
   a longitudinal, centrally disposed lumen extending through the member, the lumen adapted to convey a fluid through the member to be discharged through an outlet port disposed in a distal portion of the member;
   a selectively deployable cutting electrode positioned within the lumen, the cutting electrode being able to operably extend from the lumen upon deployment, the electrode being of such diameter that it does not fully occlude the lumen;
   a means for delivering electrosurgical energy through the device to the cauterization electrode;
   a fluid supply reservoir in fluid communication with the lumen;
   a means for delivering fluid from the reservoir to the lumen; and
   means for controlling the delivery of electrosurgical energy to the cauterization electrode to cauterize tissue.

14. The system of claim 13 further comprising a selectively deployable cutting electrode positioned within the lumen and adapted to operably extend from the lumen upon deployment, and where the means for delivering electrosurgical energy further delivers energy to the cutting electrode.

15. The system of claim 14 further comprising first and second cauterization electrodes.

16. The system of claim 15 wherein the first and second cauterization electrodes are electrically isolated from one another and adapted to effect bipolar cauterization wherein the first electrode serves as an active, energy delivering electrode and the second electrode serves as a ground electrode.

17. The system of claim 16 wherein the first and second cauterization electrodes are each helically oriented and disposed about the surface of a distal portion of the member.

18. The system of claim 14 wherein the current delivered through the cutting electrode is in the range of 0.2 to 3 amps.

19. The system of claim 18 wherein the voltage delivered through the cutting electrodes is in the range of 60 to 1000 volts RMS.

20. The system of claim 14 wherein the current delivered through the coagulation electrode is in the range of 0.25 to 1 amp.

21. The system of claim 20 wherein the voltage delivered through the coagulation electrode is in the range of 10 to 50 volts RMS.

* * * * *